(12) United States Patent
Saadat et al.

(10) Patent No.: US 8,562,516 B2
(45) Date of Patent: Oct. 22, 2013

(54) METHODS AND APPARATUS FOR OBTAINING ENDOLUMINAL ACCESS

(75) Inventors: Vahid Saadat, Saratoga, CA (US); John A. Cox, Macungie, PA (US); Chris Rothe, San Jose, CA (US)

(73) Assignee: USGI Medical Inc., San Clemente, CA (US)

(*) Notice: Subject to any disclaimer, the term of this patent is extended or adjusted under 35 U.S.C. 154(b) by 996 days.

(21) Appl. No.: 11/036,029

(22) Filed: Jan. 14, 2005

(65) Prior Publication Data

US 2005/0234294 A1    Oct. 20, 2005

(51) Int. Cl.
*A61B 1/00* (2006.01)

(52) U.S. Cl.
USPC ........... 600/129; 600/106; 600/111; 600/127; 600/166; 600/173

(58) Field of Classification Search
USPC ................ 600/101, 104, 114; 606/32–58
See application file for complete search history.

(56) References Cited

U.S. PATENT DOCUMENTS

| | | | |
|---|---|---|---|
| 5,305,121 A | 4/1994 | Molli | |
| 5,954,731 A | 9/1999 | Yoon | |
| 5,984,932 A | 11/1999 | Yoon | |
| 5,993,466 A | 11/1999 | Yoon | |
| 6,017,358 A | 1/2000 | Yoon et al. | |
| 6,066,090 A | 5/2000 | Yoon | |
| 6,086,601 A | 7/2000 | Yoon | |
| 6,277,064 B1 | 8/2001 | Yoon | |
| 6,352,503 B1 | 3/2002 | Matsui et al. | |
| 6,761,685 B2 | 7/2004 | Adams et al. | |
| 6,783,491 B2 | 8/2004 | Saadat et al. | |
| 6,790,173 B2 | 9/2004 | Saadat et al. | |
| 6,811,532 B2 | 11/2004 | Ogura et al. | |
| 6,821,285 B2 | 11/2004 | Laufer et al. | |
| 6,835,199 B2 | 12/2004 | McGuckin, Jr. et al. | |
| 6,837,847 B2 | 1/2005 | Ewers et al. | |
| 6,837,849 B2 | 1/2005 | Ogura et al. | |
| 6,899,673 B2 | 5/2005 | Ogura et al. | |
| 6,942,613 B2 | 9/2005 | Ewers et al. | |
| 6,960,162 B2 | 11/2005 | Saadat et al. | |
| 6,960,163 B2 | 11/2005 | Ewers et al. | |
| 6,991,602 B2 | 1/2006 | Nakazawa et al. | |
| 7,041,052 B2 | 5/2006 | Saadat et al. | |

(Continued)

FOREIGN PATENT DOCUMENTS

| | | |
|---|---|---|
| EP | 1585428 | 9/2005 |
| EP | 1583462 | 10/2005 |

(Continued)

OTHER PUBLICATIONS

Mason, "Development of Future of Gastroplasties for Morbid Obesity," *Arch Surg*, vol. 138 (Apr. 2003), pp. 362-366.

*Primary Examiner* — Matthew J Kasztejna
(74) *Attorney, Agent, or Firm* — Kenneth H. Ohriner; Perkins Coie LLP

(57) ABSTRACT

The present invention provides methods and apparatus for obtaining endoluminal access. An elongate body is configured for insertion within a body lumen, conduit, organ, orifice, passageway or cavity, the elongate body having a working axis and a distal region, and an articulating element disposed near the distal region, the articulating element configured to articulate off-axis from the working axis of the elongate body. The elongate may achieve access in an endoluminal or a laparoscopic fashion. Methods of using the apparatus are also provided.

27 Claims, 11 Drawing Sheets

(56) References Cited

U.S. PATENT DOCUMENTS

| | | |
|---|---|---|
| 7,128,708 B2 | 10/2006 | Saadat et al. |
| 7,160,312 B2 | 1/2007 | Saadat |
| 2002/0120253 A1 | 8/2002 | Ouchi |
| 2003/0109892 A1* | 6/2003 | Deem et al. ............... 606/151 |
| 2004/0059346 A1 | 3/2004 | Adams et al. |
| 2004/0116897 A1 | 6/2004 | Aboul-Hosn |
| 2004/0116949 A1 | 6/2004 | Ewers et al. |
| 2004/0122290 A1 | 6/2004 | Irion et al. |
| 2004/0122456 A1 | 6/2004 | Saadat et al. |
| 2004/0122473 A1 | 6/2004 | Ewers et al. |
| 2004/0138525 A1 | 7/2004 | Saadat et al. |
| 2004/0138529 A1 | 7/2004 | Wiltshire et al. |
| 2004/0147958 A1 | 7/2004 | Lam et al. |
| 2004/0162568 A1 | 8/2004 | Saadat et al. |
| 2004/0167546 A1 | 8/2004 | Saadat et al. |
| 2004/0186349 A1 | 9/2004 | Ewers et al. |
| 2004/0193117 A1 | 9/2004 | Laufer et al. |
| 2004/0193184 A1 | 9/2004 | Laufer et al. |
| 2004/0193193 A1 | 9/2004 | Laufer et al. |
| 2004/0193194 A1 | 9/2004 | Laufer et al. |
| 2004/0194790 A1 | 10/2004 | Laufer et al. |
| 2004/0210243 A1 | 10/2004 | Gannoe et al. |
| 2004/0215216 A1 | 10/2004 | Gannoe et al. |
| 2004/0225183 A1 | 11/2004 | Michlitsch et al. |
| 2004/0225305 A1 | 11/2004 | Ewers et al. |
| 2004/0243152 A1 | 12/2004 | Taylor et al. |
| 2004/0249362 A1 | 12/2004 | Levine et al. |
| 2004/0249367 A1 | 12/2004 | Saadat et al. |
| 2005/0020901 A1 | 1/2005 | Belson et al. |
| 2005/0033320 A1 | 2/2005 | McGuckin, Jr. et al. |
| 2005/0033328 A1 | 2/2005 | Laufer et al. |
| 2005/0043758 A1 | 2/2005 | Golden et al. |
| 2005/0049617 A1 | 3/2005 | Chatlynne et al. |
| 2005/0065397 A1 | 3/2005 | Saadat et al. |
| 2005/0065401 A1 | 3/2005 | Saadat et al. |
| 2005/0065536 A1 | 3/2005 | Ewers et al. |
| 2005/0075653 A1 | 4/2005 | Saadat et al. |
| 2005/0096502 A1 | 5/2005 | Khalili |
| 2005/0107663 A1 | 5/2005 | Saadat et al. |
| 2005/0113640 A1 | 5/2005 | Saadat et al. |
| 2005/0119524 A1 | 6/2005 | Sekine et al. |
| 2005/0119671 A1 | 6/2005 | Reydel et al. |
| 2005/0137455 A1 | 6/2005 | Ewers et al. |
| 2005/0165272 A1 | 7/2005 | Okada et al. |
| 2005/0192629 A1 | 9/2005 | Saadat et al. |
| 2005/0203488 A1 | 9/2005 | Michlitsch et al. |
| 2005/0203489 A1 | 9/2005 | Saadat et al. |
| 2005/0203500 A1 | 9/2005 | Saadat et al. |
| 2005/0222495 A1 | 10/2005 | Okada et al. |
| 2005/0228224 A1 | 10/2005 | Okada et al. |
| 2005/0234294 A1 | 10/2005 | Saadat et al. |
| 2005/0234296 A1 | 10/2005 | Saadat et al. |
| 2005/0245945 A1 | 11/2005 | Ewers et al. |
| 2005/0250980 A1 | 11/2005 | Swanstrom et al. |
| 2005/0250984 A1 | 11/2005 | Lam et al. |
| 2005/0250985 A1 | 11/2005 | Saadat et al. |
| 2005/0250986 A1 | 11/2005 | Rothe et al. |
| 2005/0250987 A1 | 11/2005 | Ewers et al. |
| 2005/0250988 A1 | 11/2005 | Ewers et al. |
| 2005/0250990 A1 | 11/2005 | Le et al. |
| 2005/0251091 A1 | 11/2005 | Saadat et al. |
| 2005/0251157 A1 | 11/2005 | Saadat et al. |
| 2005/0251158 A1 | 11/2005 | Saadat et al. |
| 2005/0251159 A1 | 11/2005 | Ewers et al. |
| 2005/0251160 A1 | 11/2005 | Saadat et al. |
| 2005/0251161 A1 | 11/2005 | Saadat et al. |
| 2005/0251162 A1 | 11/2005 | Rothe et al. |
| 2005/0251165 A1 | 11/2005 | Vaughan et al. |
| 2005/0251166 A1 | 11/2005 | Vaughan et al. |
| 2005/0251176 A1 | 11/2005 | Swanstrom et al. |
| 2005/0251177 A1 | 11/2005 | Saadat et al. |
| 2005/0251189 A1 | 11/2005 | Saadat et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267335 A1 | 12/2005 | Okada et al. |
| 2005/0272977 A1 | 12/2005 | Saadat et al. |
| 2005/0277945 A1 | 12/2005 | Saadat et al. |
| 2005/0277966 A1 | 12/2005 | Ewers et al. |
| 2005/0277975 A1 | 12/2005 | Saadat et al. |
| 2005/0277981 A1 | 12/2005 | Maahs et al. |
| 2005/0277983 A1 | 12/2005 | Saadat et al. |
| 2006/0009789 A1 | 1/2006 | Gambale et al. |
| 2006/0020274 A1 | 1/2006 | Ewers et al. |
| 2006/0020276 A1 | 1/2006 | Saadat et al. |
| 2006/0058582 A1 | 3/2006 | Maahs et al. |
| 2006/0100480 A1 | 5/2006 | Ewers et al. |
| 2006/0100579 A1 | 5/2006 | Maahs et al. |
| 2006/0111614 A1 | 5/2006 | Saadat et al. |
| 2006/0135971 A1 | 6/2006 | Swanstrom et al. |
| 2006/0157067 A1 | 7/2006 | Saadat et al. |
| 2006/0161185 A1 | 7/2006 | Saadat et al. |
| 2006/0178560 A1 | 8/2006 | Saadat et al. |
| 2006/0178562 A1 | 8/2006 | Saadat et al. |
| 2006/0183975 A1 | 8/2006 | Saadat et al. |
| 2006/0184161 A1 | 8/2006 | Maahs et al. |
| 2006/0189845 A1 | 8/2006 | Maahs et al. |
| 2006/0217762 A1 | 9/2006 | Maahs et al. |
| 2006/0237022 A1 | 10/2006 | Chen et al. |
| 2006/0237023 A1 | 10/2006 | Cox et al. |
| 2006/0258909 A1 | 11/2006 | Saadat et al. |
| 2006/0271073 A1 | 11/2006 | Lam et al. |
| 2006/0271074 A1 | 11/2006 | Ewers et al. |
| 2006/0271101 A1 | 11/2006 | Saadat et al. |
| 2006/0287666 A1 | 12/2006 | Saadat et al. |
| 2007/0015965 A1 | 1/2007 | Cox et al. |
| 2007/0079924 A1 | 4/2007 | Saadat et al. |
| 2007/0123840 A1 | 5/2007 | Cox |
| 2007/0142849 A1 | 6/2007 | Ewers et al. |

FOREIGN PATENT DOCUMENTS

| | | |
|---|---|---|
| EP | 1648279 | 4/2006 |
| EP | 1699366 | 9/2006 |
| EP | 1781184 | 5/2007 |
| EP | 1804680 | 7/2007 |
| EP | 1804683 | 7/2007 |
| EP | 1863389 | 12/2007 |
| EP | 1868484 | 12/2007 |
| JP | 06-054796 A | 3/1994 |
| JP | 2006-512935 | 4/2006 |
| JP | 2007-513717 | 5/2007 |
| JP | 2007-521033 | 8/2007 |
| JP | 2007-532240 | 11/2007 |
| WO | WO 02/060328 A1 | 8/2002 |
| WO | WO 03/092509 A1 | 11/2003 |
| WO | WO 03/094785 A1 | 11/2003 |
| WO | WO 2004/019788 A2 | 3/2004 |
| WO | WO 2004/021894 A1 | 3/2004 |
| WO | WO 2004/041119 | 5/2004 |
| WO | WO 2004/004542 A2 | 6/2004 |
| WO | WO 2004/064600 | 8/2004 |
| WO | WO 2004/084808 A2 | 10/2004 |
| WO | WO 2004/103430 | 12/2004 |
| WO | WO 2004/110285 A1 | 12/2004 |
| WO | WO 2005/011463 | 2/2005 |
| WO | WO 2005/011519 | 2/2005 |
| WO | WO 2005/037152 A1 | 4/2005 |
| WO | WO 2005/048815 A3 | 6/2005 |
| WO | WO 2005/050971 A2 | 6/2005 |
| WO | WO 2005/053517 A1 | 6/2005 |
| WO | WO 2005/058239 | 6/2005 |
| WO | WO 2005/086945 | 9/2005 |
| WO | WO 2005/104927 | 11/2005 |
| WO | WO 2005/110244 | 11/2005 |
| WO | WO 2005/122914 | 12/2005 |
| WO | WO 2005/122915 | 12/2005 |
| WO | WO 2006/019868 | 2/2006 |
| WO | WO 2006/039199 | 4/2006 |
| WO | WO 2006/039223 | 4/2006 |

(56) References Cited

FOREIGN PATENT DOCUMENTS

| WO | WO 2006/039296 | 4/2006 |
| WO | WO 2006/078429 | 7/2006 |
| WO | WO 2006/089217 | 8/2006 |
| WO | WO 2006/093975 | 9/2006 |
| WO | WO 2006/110275 | 10/2006 |
| WO | WO 2006/127306 | 11/2006 |
| WO | WO 2007/009021 | 1/2007 |

\* cited by examiner

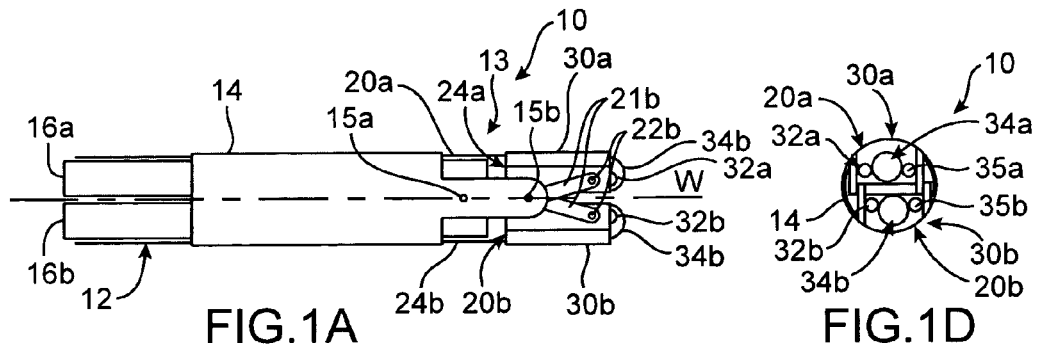
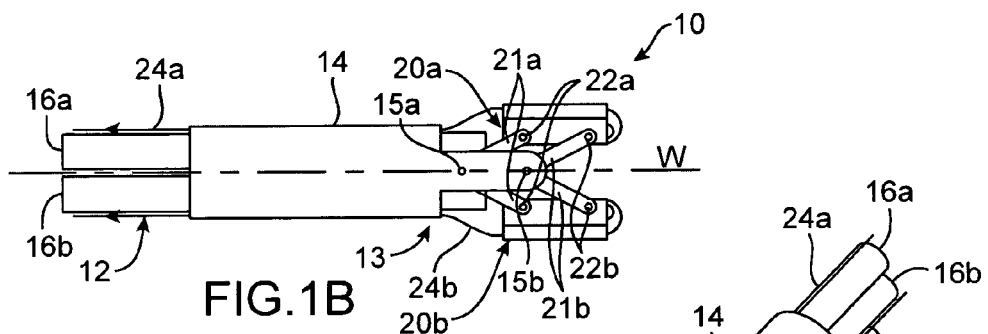
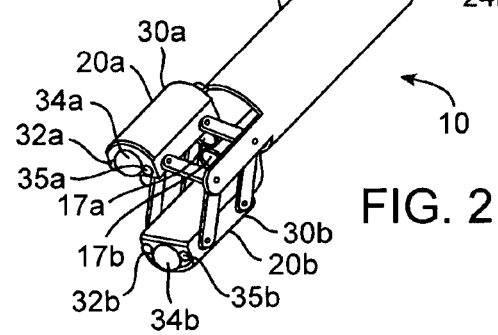
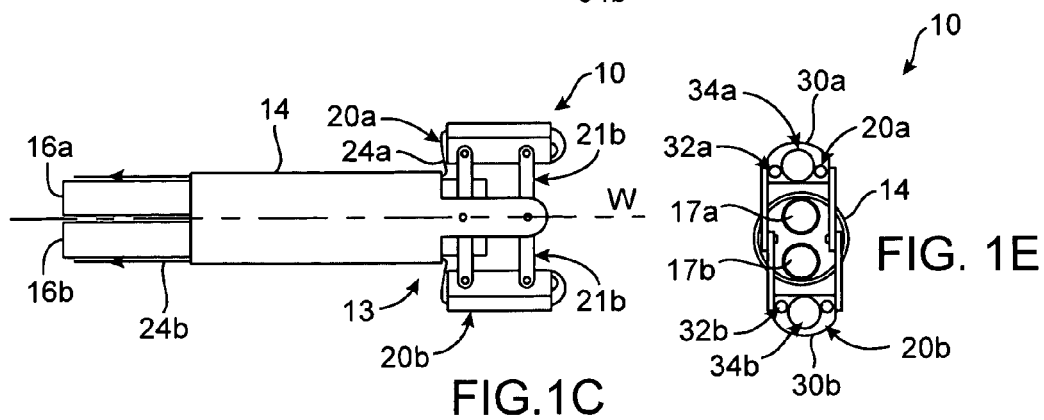

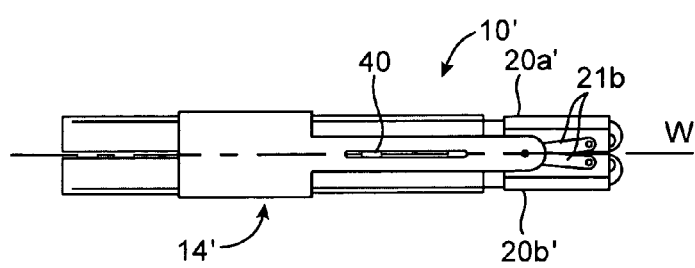
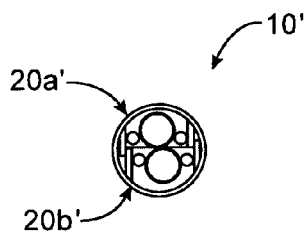
FIG. 3A       FIG. 3D
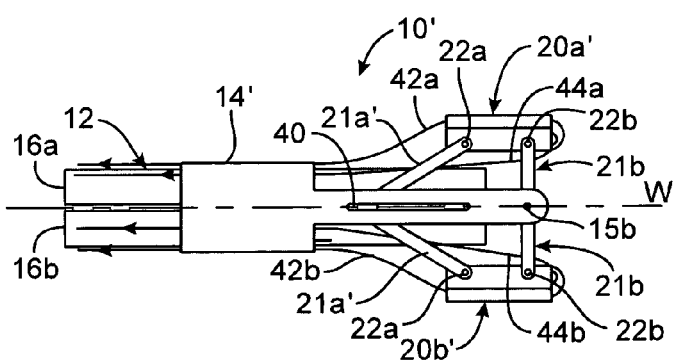
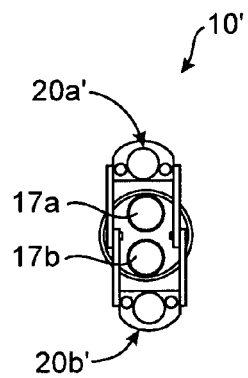
FIG. 3B       FIG. 3E
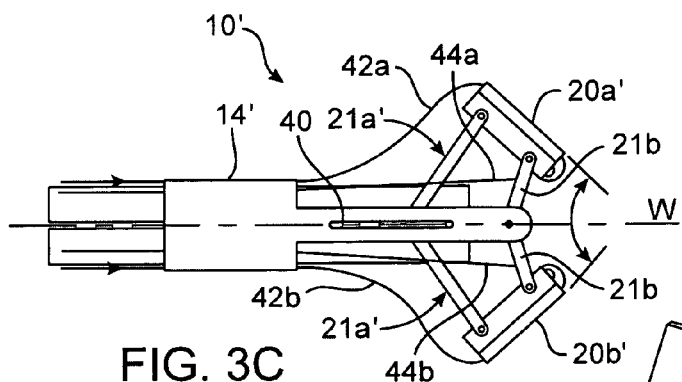
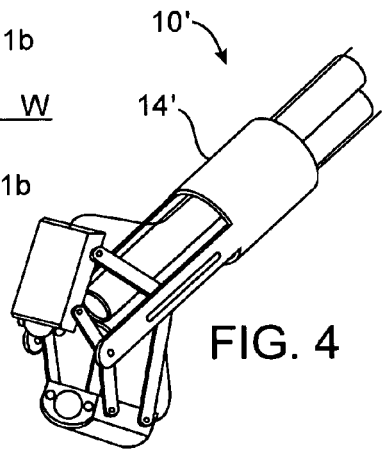
FIG. 3C       FIG. 4

METHODS AND APPARATUS FOR OBTAINING ENDOLUMINAL ACCESS

CROSS-REFERENCES TO RELATED APPLICATIONS

The present application is related to, but does not claim priority from, U.S. patent application Ser. No. 10/824,936, filed Apr. 14, 2004, which is incorporated herein by reference in its entirety.

BACKGROUND OF THE INVENTION

Field of the Invention

The present invention relates to methods and apparatus for obtaining endoluminal access. More particularly, the present invention relates to methods and apparatus for obtaining endoluminal access utilizing off-axis articulation.

Medical endoscopy entails the insertion of an elongate body into a body lumen, conduit, organ, orifice, passageway, etc. The elongate body typically has a longitudinal or working axis and a distal region, and a visualization element disposed near the distal region in-line with the working axis. The visualization element may comprise an optical fiber that extends through the elongate body, or a video chip having an imaging sensor, the video chip coupled to or including a signal-processing unit that converts signals obtained by the imaging sensor into an image. The elongate body may also include a working lumen to facilitate passage of diagnostic or therapeutic tools therethrough, or for injection of fluids or to draw suction.

The maximum delivery profile for a medical endoscope may be limited by the cross-sectional profile of the body lumen, conduit, organ, orifice, passageway, etc., in which the endoscope is disposed. At the same time, advances in therapeutic endoscopy have led to an increase in the complexity of operations attempted with endoscopes, as well as the complexity of tools advanced through the working lumens of endoscopes. As tool complexity has increased, a need has arisen in the art for endoscopes having relatively small delivery profiles that allow access through small body lumens, but that have relatively large working lumens that enable passage of complex diagnostic or therapeutic tools. Furthermore, as the complexity of operations attempted with endoscopes has increased, there has arisen a need for enhanced visualization platforms, including three-dimensional or stereoscopic visualization platforms.

As with endoscopy, ever more challenging procedures are being conducted utilizing laparoscopic techniques. Due to, among other factors, the profile of instruments necessary to perform these procedures, as well as a need to provide both visualization and therapeutic instruments, laparascopic procedures commonly require multiple ports to obtain the necessary access. Multiple ports also may be required due to the limited surgical space accessible with current, substantially rigid straight-line laparoscopic instruments.

In view of the foregoing, it would be desirable to provide methods and apparatus for obtaining endoluminal access that facilitate introduction of the apparatus into relatively small body lumens, while providing for introduction of at least one relatively large tool, as compared to standard endoscopes or laparoscopes. It also would be desirable to provide methods and apparatus that facilitate single port laparoscopy.

BRIEF SUMMARY OF THE INVENTION

Endoluminal access that facilitates introduction of the apparatus into relatively small body lumens while providing for introduction of at least one relatively large tool, as compared to a standard endoscope or laparoscope, may be accomplished by providing an elongate body configured for insertion within a body lumen, conduit, organ, orifice, passageway, etc. The elongate body has a working or main longitudinal axis and a distal region, and at least one articulating element disposed near or at the distal region. The articulating element generally is configured to articulate off-axis or out-of-line from the working axis of the elongate body such that the element (or elements) are extendable and retractable in a radial direction relative to the working axis. The element may comprise, for example, the distal region of a working lumen extending through the elongate body; a visualization element, such as a fiber optic or video chip; a diagnostic or therapeutic tool; or an illumination element. Additional alternative articulating elements will be apparent to one of skill in the art.

The articulating elements may alternatively or additionally provide radially extendable platforms from which various tools may be advanced and/or therapies may be conducted. This extendable platform may allow the user to deploy the elements once the apparatus has been desirably situated within the body giving the user a versatile platform from which to access a greater portion of the body lumen while maintaining a device having a relatively small delivery profile.

Advantageously, the articulating element provides the elongate body with a collapsed delivery configuration and a radially expanded deployed configuration. The collapsed delivery profile may facilitate passage of the elongate body within small body lumens, cavities, etc., while the expanded deployed profile may facilitate diagnosis or therapy via the elongate body once the elongate body is disposed within the body lumen. For example, off-axis articulation of the articulating element may expose distal openings of one or more working lumens extending through the elongate body.

With traditional endoscopes or laparoscopes, a maximum profile of the working lumen is constrained by geometry of the visualization element. Conversely, the apparatus described herein enables one or more visualization elements, working lumens, tools, illumination elements, etc., to be aligned with the working axis of the elongate body in the delivery configuration, and articulated out of alignment in the radially deployed configuration, thereby significantly reducing geometric constraints. As will be apparent, the working lumen(s), tool(s), illumination elements and visualization element(s) optionally may be provided as part of multiple distinct devices. For example, a standard endoscope or laparoscope may be provided as a visualization element, while one or more working lumens may be disposed within an overtube or endoluminal tool deployment system (e.g., as described in Applicant's co-pending U.S. patent application Ser. No. 10/797,485, filed Mar. 9, 2004, which is incorporated herein by reference in its entirety) disposed over the standard endoscope/laparoscope. Apparatus of the present invention additionally or alternatively may be advanced through a trocar or multi-lumen insert, as described, for example, in Applicant's co-pending U.S. patent application Ser. No. 10/843,682, filed May 10, 2004, which is incorporated herein by reference in its entirety.

Optionally, multiple articulating elements may be provided near the distal region of the elongate body. When the multiple articulating elements comprise two or more visualization elements, stereoscopic visualization may be provided. When the multiple elements comprise multiple working lumens or tools, complex therapeutic or diagnostic endoluminal procedures may be performed. Combinations of various articulating elements may be provided.

When used in conjunction with laparoscopic endoluminal access, off-axis articulating element(s) may facilitate achievement of complex diagnostic and/or therapeutic laparoscopic procedures through a single port or opening. Likewise, when utilized for endoscopic endoluminal access, the articulating element(s) may facilitate otherwise unachievable endoscopic procedures. Thus, off-axis articulating element(s) may enable a transition of procedures currently performed in an open surgical fashion or via multiple laparoscopic ports to less invasive endoscopic or laparoscopic techniques. It is expected that the element(s) also may facilitate novel procedures that may not be performed utilizing current methods and apparatus.

It should be understood that, in addition to obtaining endoluminal access, the apparatus and methods described herein also may be utilized to obtain access to non-luminal spaces, regions, or cavities within a patient, for example, to the patient's peritoneum.

BRIEF DESCRIPTION OF THE DRAWINGS

FIGS. 1A-1E are side and frontal views of one variation of the apparatus, illustratively showing the articulating elements in collapsed delivery configurations, partially articulated configurations and expanded deployed configurations;

FIG. 2 is a perspective view of the apparatus of FIG. 1C;

FIGS. 3A-3E are side and frontal views of an alternative variation of the apparatus of FIGS. 1A-1C; shown, respectively, in collapsed, partially articulated, and expanded configurations;

FIG. 4 is a perspective view of the apparatus of FIG. 3C;

DETAILED DESCRIPTION OF THE INVENTION

Figure 5:
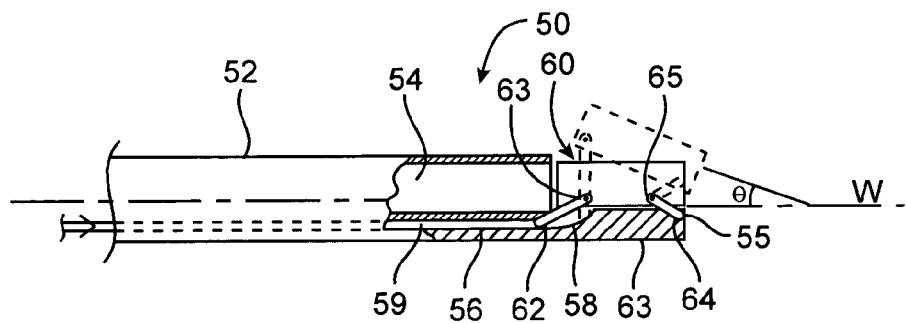
FIG. 5 is a schematic side view, partially in cut-away section, of an alternative variation comprising articulation biasing.

Endoluminal access may be achieved more effectively by utilizing off-axis articulation with an apparatus advanced within a body lumen, e.g., advanced endoluminally or laparoscopically within the body lumen. As described herein, off-axis articulating elements may act as radially extendable platforms from which various tools may be advanced or therapies may be conducted. This extendable platform may allow the user to deploy the elements once the apparatus has been desirably situated within the body, thereby giving the user a versatile platform from which to access a greater portion of the body lumen while maintaining a device having a relatively small delivery profile.

With reference to FIGS. 1 and 2, a first variation of the apparatus is shown. Apparatus 10 comprises elongate body 12 configured for insertion within a body lumen, conduit, organ, orifice or passageway, e.g., via laparoscopic or endoluminal techniques. Body 12 comprises working axis W and distal region 13. The elongate body may, for example, comprise a flexible, steerable, rigidizable and/or multi-segmented body, such as described in Applicant's co-pending U.S. patent application Ser. No. 10/797,485, filed Mar. 9, 2004, which has been incorporated by reference above. Body 12 alternatively may be substantially rigid and/or straight-line, and may be configured for laparoscopic access to the body lumen, etc. As will be apparent, flexible, steerable and/or rigidizable instruments may be advanced laparoscopically or endoluminally. Laparoscopic surgical techniques are described, for example, in Applicant's co-pending U.S. patent application Ser. No. 10/843,682, filed May 10, 2004, which has been incorporated by reference above.

Apparatus 10 also comprises at least one articulating element 20, shown in this example as two elements 20a and 20b (collectively referred to as elements 20), disposed near or at distal region 13 of body 12. Elongate body 12 further comprises housing 14, which may be slidably disposed over one or more working lumens 16, illustratively shown as working lumens 16a and 16b. Articulating elements 20 may be pivotally coupled to housing 14 by linkages 21a and 21b, which extend between hinges 22a and 22b of elements 20a and 20b and hinges 15a and 15b, respectively, of housing 14. Push/pull members 24a and 24b also may be provided to actuate articulating elements 20a and 20b, respectively, between the collapsed profile and radially extended profile.

Members 24a and 24b may extend along elongate body 12, for example, between housing 14 and lumens 16, to a proximal region of the elongate body (not shown) for manipulation by a medical practitioner. The members may be coupled to one another for coordinated actuation of articulating elements 20, or may be decoupled for independent actuation. Furthermore, the members may comprise cables or coils, as described hereinafter, adapted to convey control elements between the articulating elements and the elongate body.

As seen in FIGS. 1 and 2, articulating elements 20 are configured to articulate off-axis or out-of-line from working axis W of elongate body 12. FIG. 1A shows articulating elements 20 in a collapsed delivery configuration having a reduced delivery profile suited for delivery within a body orifice, lumen, cavity, etc. FIG. 1B shows articulating elements 20 in a partially articulated configuration. FIGS. 1C and 2 show the articulating elements fully articulated to a deployed configuration of expanded profile.

Articulating elements 20 may be articulated from the reduced profile of FIGS. 1A and 1D to the expanded profile of FIGS. 1C and 1E by retracting members 24 relative to housing 14. The articulating elements may be articulated back to the collapsed profile, as desired, by advancing members 24 relative to housing 14. As will be apparent, elements 20 alternatively may be articulated by advancing or retracting housing 14 relative to members 24.

As seen in FIGS. 1C and 2, articulation of elements 20 to the expanded deployed configuration advantageously exposes distal openings 17a and 17b of working lumens 16a and 16b, respectively. In the delivery configuration of FIG. 1A, the lumens and articulating elements are aligned with working axis W of elongate body 12. Such alignment reduces the delivery profile of apparatus 10, but also causes articulating elements 20 to be disposed in-line with lumens 16, thereby blocking distal openings 17 of the lumens.

Articulating elements 20 off-axis and out of alignment with working axis W exposes distal openings 17 of lumens 16. Once exposed, lumens 16 may be used for passage of diagnostic or therapeutic tools from the proximal to the distal region of apparatus 10, as well as to draw suction, inject fluids, etc. By providing apparatus 10 with elements that articulate, lumens 16 may be provided with larger cross-sectional profiles than otherwise would be possible for a given delivery profile, as compared to apparatus having needed elements that cannot articulate.

Each articulating element 20 may comprise, for example, the distal region of a working lumen extending through elongate body 12. Alternatively, each articulating element may comprise a visualization element, such as a fiber optic or video chip. As yet another alternative, each articulating element may comprise a diagnostic or therapeutic tool, or an illumination element. Additional alternative articulating elements will be apparent.

In FIGS. 1 and 2, articulating elements 20 illustratively comprise visualization elements 30a and 30b. Elements 30 may comprise illumination sources 32a and 32b, as well as optics 34a and 34b. Optional illumination sources 32 may be used to provide light for imaging with elements 30, while optics 34 may, for example, comprise lenses, filters, etc. The optics may be coupled to one or more optical fibers and/or video chips that transmit visual information to a proximal region of apparatus 10. Optional flushing elements 35 also may be provided. Control elements for visualization elements 30, such as electrical wires, flushing lumens, etc., may run within or along push/pull members 24.

When video chips having imaging sensors are coupled to optics 34, the chips may be adapted to receive, as well as to transmit and/or signal process, visual information. Illustrative imaging sensors that may be used as part of visualization elements 30 include, but are not limited to, charge coupled device ("CCD") image sensors, complementary metal oxide semiconductor ("CMOS") image sensors, multi-layer solid state image sensors, direct image sensors, and combinations thereof. The video chips may wirelessly transmit signals to a processing and/or display unit, or one or more wires may extend along the length of the elongate body to carry such signals.

Since apparatus 10 has two articulating visualization elements 30, the apparatus 10 is adapted to provide stereoscopic or 3-dimensional visualization. Stereoscopic visualization may be displayed to a medical practitioner, for example, via a viewfinder disposed in front of the practitioner's eyes or via a standard monitor. A depth of field, a focal point or depth, and/or a field of view of stereoscopic images produced with visualization elements 30 may be altered, for example, by changing a degree of articulation of elements 30, by varying parameters of optics 34, via digital signal processing techniques, etc.

Referring now to FIGS. 3 and 4, an alternative variation of apparatus 10 is described. Apparatus 10' comprises housing 14' having at least one slot 40. Linkages 21a' extend between hinges 22a of elements 20' and slot 40 of housing 14'. In this variation, linkages 21a' are longer than more distal linkages 21b, and are slidably disposed within slot 40 of the housing. Apparatus 10' further comprises proximal push/pull members 42a and 42b coupled to the proximal regions of articulating elements 20a and 20b, respectively, as well as distal push/pull members 44a and 44b coupled to the distal regions of elements 20.

As seen in FIGS. 3A-3E, actuation of articulating elements 20a' and 20b' may be achieved by coordinated movements of proximal members 42a and 42b, distal members 44a and 44b and housing 14'. In FIGS. 3A and 3D, apparatus 10' is disposed in the collapsed delivery configuration suitable for advancement within a body lumen. In FIG. 3B, members 42a and 42b, as well as members 44a and 44b, have been retracted relative to housing 14'. This causes long linkages 21a' to articulate about hinges 22a of elements 20' and slide proximally within slot 40 of housing 14', while linkages 21b articulate about hinges 15b and 22b. Elements 20a' and 20b' articulate out of alignment and off-axis from working axis W of elongate body 12, thereby exposing distal openings 17a and 17b of lumens 16a and 16b.

As seen in FIGS. 3C, 3E and 4, subsequent advancement of proximal members 42a and 42b relative to housing 14' and distal members 44a and 44b causes long linkages 21a' to slide distally within slot 40 and articulate about hinges 22a. Such movement causes the distal regions of elements 20' to articulate inwards relative to the proximal regions of the elements, thereby changing the relative angle between elements 20a' and 20b'. As will be apparent, elements 20a' and 20b' may be articulated in either a coordinated fashion or individually.

When elements 20a' and 20b' comprise visualization elements (optionally used in a stereoscopic fashion), relative angulation of the elements may be used to dynamically alter a focal point or depth, a depth of field and/or a field of view provided by the elements. When the elements comprise tools (e.g. grasping tool arms, cutting tools, plicating tools, affixing tools, etc.) or lumens, the tools or lumens may be angled for better positioning of the tools/lumens. When the elements comprise illumination elements, angling or angulation of the elements may better light a region of interest. As will be apparent, any combination of various articulating and/or angulate-able elements 20 may be provided, including combinations of visualization elements, illumination elements, tools, lumens, etc.

Referring now to FIG. 5, an alternative variation is described comprising articulation biasing. Apparatus 50 comprises elongate body 52 having working axis W, distal region 53, working lumen 54, control lumen 56 and ramp 58. Apparatus 50 may further comprise articulating element 60 disposed near or at distal region 53 of body 52. Articulating element 60 is coupled to elongate body 52 by proximal linkage 62 and torsion spring 64. Linkage 62 extends between hinge 63 of articulating element 60 and control rod 59 disposed within control lumen 56 of body 52. Torsion spring 64 extends between hinge 65 of the articulating element and hinge 55 of the elongate body. Torsion spring 64 provides element 60 with articulation biasing. In other variations, other biasing elements aside from torsion springs may be utilized.

As seen in dotted profile in FIG. 5, advancement of control rod 59 relative to elongate body 52 advances linkage 62 along ramp 58 and articulates element 60, thereby exposing the distal end of lumen 54. Torsion spring 64 has a natural tendency to push element 60 off-axis and biases the element to the articulated position. Once element 60 has 'sprung-up' to the articulated position, further advancement of rod 59 controls the angle Θ of element 60 relative to elongate body 52. Retraction of rod 59 may overcome the articulation biasing of spring 64 and return apparatus 50 to the collapsed delivery configuration. The spring constant of torsion spring 64 may be specified to control a degree of articulation biasing provided by the spring.

Figure 6:
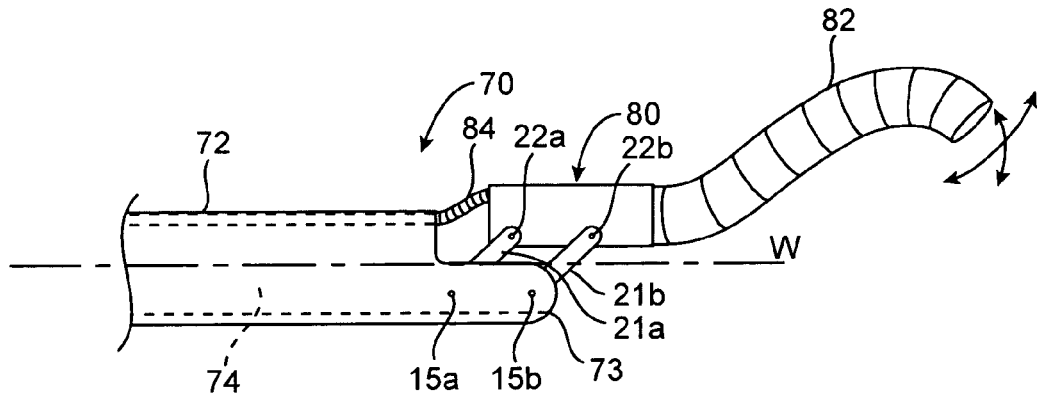
FIG. 6 is a schematic side view of an alternative variation comprising an articulating element having a steerable shaft.

Referring now to FIG. 6, another variation is described wherein the articulating element comprises a steerable shaft. Apparatus 70 comprises elongate body 72 having working axis W, distal region 73 and lumen 74. Apparatus 70 further comprises articulating element 80 disposed near distal region 73 of elongate body 72. Element 80 is coupled to the elongate body by previously-described linkages 21 disposed between hinges 15 and 22.

Articulating element 80 comprises steerable shaft 82. Shaft 82 may be passively articulate-able or, alternatively, may be actively controllable. Any number of conventional methods may be utilized to articulate the shape and configuration of shaft 82. In FIG. 6, shaft 82 illustratively may, for example, be steerable in any number of directions. In this variation, shaft 82 may be steerable in at least four directions, e.g., via four control wires routed through or along cable 84 and elongate body 72 to a proximal region of apparatus 70 for manipulation by a medical practitioner. Cable 84 may also be used to articulate element 80. As discussed hereinbelow with respect to FIGS. 11 and 12, proximal of cable 84, the control wires for steerable shaft 82 preferably are routed through or along body 72 in spaces that would not be usable as working lumens or for tool insertion.

During delivery, articulating element 80 and steerable shaft 82 preferably are aligned with working axis W of elongate body 72. Advantageously, the ability to articulate element 80 off-axis post-delivery allows apparatus 70 to have both a large working lumen 74 and a small collapsed delivery profile. Furthermore, steerable shaft 82 gives the apparatus an off-axis platform with added finctionality for performing complex procedures. The steering capability of shaft 82 may be used to steer therapeutic or diagnostic tools, and/or for illumination, visualization, fluid flushing, suction, etc., into better position for conducting such procedures.

Various methods and apparatus for controlling elements used in conjunction with shaft 82 may be routed through cable 84 along with the control wires for shaft 82. For example, when a visualization element is coupled to steerable shaft 82, electrical wires may run through cable 84 for sending and/or receiving signals, power, etc., to/from the visualization element. In such a variation, the visualization element would allow direct visualization during insertion within a body lumen, while providing off-axis visualization and steering, as well as facilitating tool introduction, post-articulation. Alternatively or additionally, when a working lumen is disposed through steerable shaft 82, cable 84 may comprise a lumen for connecting the shaft lumen to a lumen extending through elongate body 72 of apparatus 70.

Figure 7:
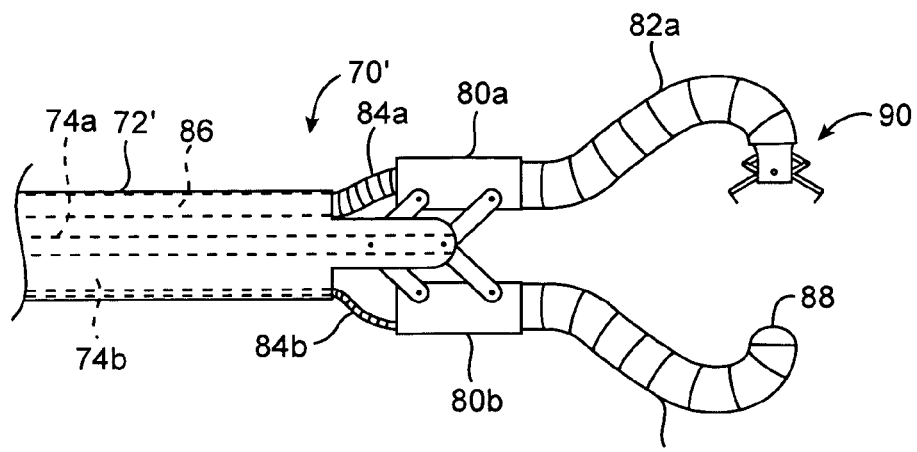
FIG. 7 is a schematic side view of an alternative variation of the apparatus of FIG. 6 comprising multiple articulating elements having steerable shafts.

Referring now to FIG. 7, an alternative variation of apparatus 70 is described comprising multiple articulating elements having steerable shafts. Apparatus 70' comprises first articulating element 80a and second articulating element 80b. Elements 80 comprise first steerable shaft 82a and second steerable shaft 82b, respectively. Lumens 74a and 74b extend through elongate body 72' and are exposed upon articulation of elements 80a and 80b, respectively. As will be apparent, a single lumen or more than two lumens alternatively may be provided. Likewise, more than two articulating elements and/or steerable shafts optionally may be provided.

In FIG. 7, first steerable shaft 82a illustratively is shown with working lumen 86 that extends through the shaft, as well as through cable 84a and elongate body 72'. Exemplary grasper tool 90 is shown advanced through lumen 86. Second steerable shaft 82b illustratively is shown with visualization element 88 coupled to an end thereof. Electrical wires, e.g., for powering and transmitting signals to/from the visualization element, are disposed within cable 84b. As will be apparent, steerable shafts 82 may be provided with additional or alternative capabilities.

Figure 8A:
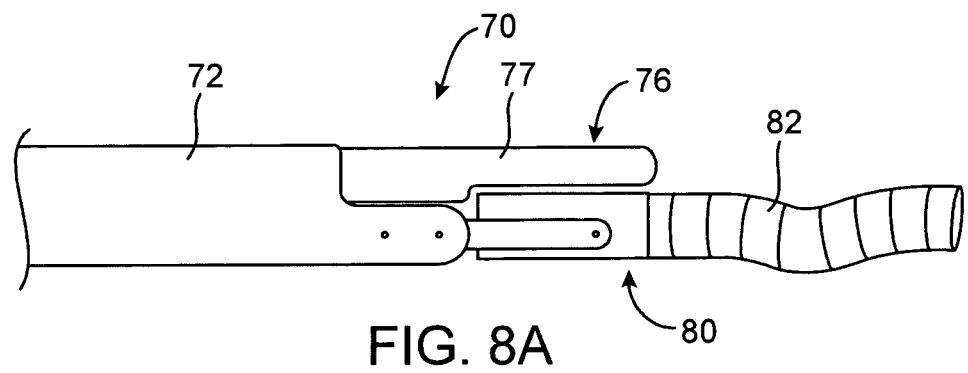
FIGS. 8A and 8B are schematic side views of illustrative variations of atraumatic tips for use with the apparatus.

With reference to FIG. 8, illustrative embodiments of atraumatic tips for use with apparatus of the present invention are described. In FIG. 8A, apparatus 70 of FIG. 6 is shown with atraumatic tip 76. Tip 76 provides a smooth transition between elongate body 72 and articulating element 80 with steerable shaft 82. Tip 76 may, for example, comprise an inflatable balloon that may be inflated as shown during insertion and delivery of apparatus 70, then deflated prior to articulation of element 80 and off-axis steering of shaft 82, so as not to block or impede articulation or the distal opening of the lumen 74 post-articulation.

Figure 8B:
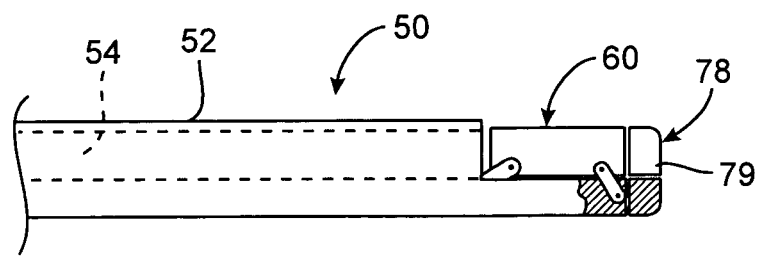

In FIG. 8B, apparatus 50 of FIG. 5 comprises alternative atraumatic tip 78 having cap 79, which optionally may be fabricated from rubber. As illustrated by the cut-away section in FIG. 8B, the cap may be U-shaped to both provide a smooth transition between elongate body 52 and articulating element 60 in the delivery configuration, as well as to ensure that the cap does not block or impede lumen 54 post-articulation.

Figure 9A:
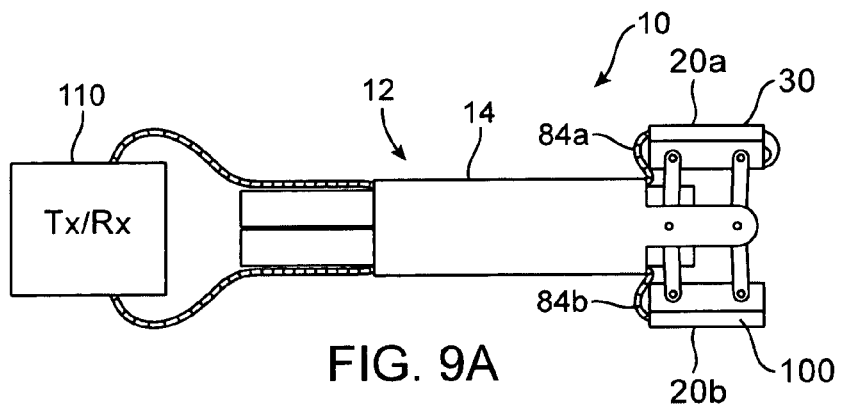
FIGS. 9A and 9B are schematic side and detail views, respectively, of a variation of the apparatus of FIGS. 1 and 2 comprising an illumination articulating element and a visualization articulating element.
Figure 9B:
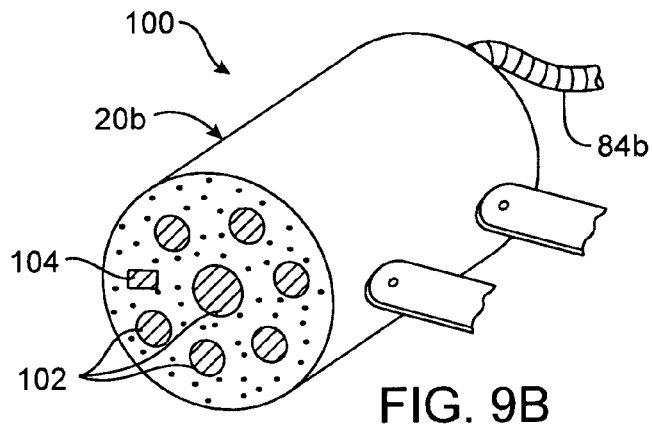

With reference now to FIGS. 9, a variation of the apparatus of FIGS. 1 and 2 is described comprising an articulating illumination element and an articulating visualization element. In FIG. 9A, articulating element 20a of apparatus 10 comprises previously described visualization articulating element 30, while articulating element 20b comprises illumination articulating element 100. Control wires for both element 30 and element 100, illustratively routed through coils or cables 84, are proximally coupled to control/power unit 110. As seen in FIG. 9B, illumination element 100 comprises at least one light emitting diode ("LED") 102, as well as optional sensor 104. Other variations may utilize other types of lights or illumination methods, e.g., incandescent lights, fluorescent lights or chemicals, etc. Control unit 110 may coordinate signals from visualization element 30 and sensor 104 to appropriately set the white balance of visualization element 30, as well as the intensity of light emitted from LEDs 102, etc.

Figure 10:
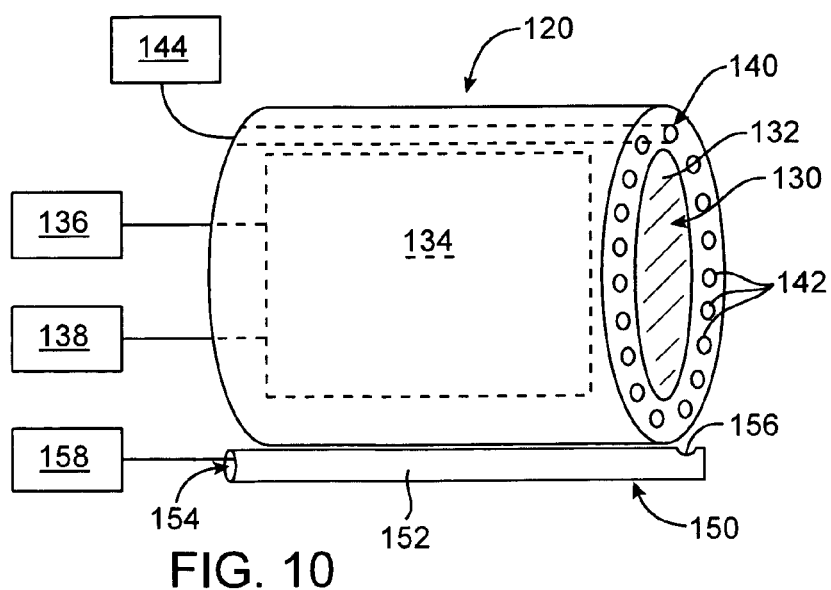
FIG. 10 is a detail view of an articulating element featuring visualization, illumination and flushing features.

With reference to FIG. 10, a combination articulating element is described that provides illumination, visualization and fluid flushing. Articulating element 120 comprises visualization element 130 having lens 132 and video chip 134 with an image sensor, such as a CCD or CMOS image sensor. The video chip is coupled to power source 136, as well as signal processing and/or display unit 138.

Element 120 further comprises illumination element 140 for illuminating a region of interest to facilitate visualization with element 130. Illumination element 140 comprises optical fibers 142, which are illustratively disposed in a ring about lens 132. Fibers 142 are coupled to light source 144.

Element 120 also comprises flushing element 150 for cleaning lens 132 of visualization element 130, as well as optical fibers 142 of illumination element 140. Flushing element 150 comprises tube 152 having lumen 154 that distally terminates at side port 156 disposed adjacent to lens 132. Tube 152 may be proximally coupled to fluid injection element 158, which may, for example, comprise a syringe filled with saline.

Figure 11:
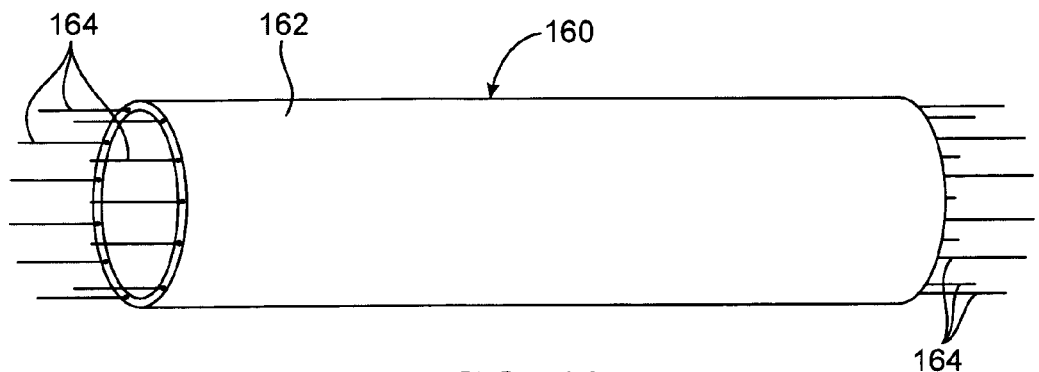
FIG. 11 is a schematic view of a liner for use with an elongate body, the liner adapted to carry control elements through the body.

Referring now to FIG. 11, a liner for use with an elongate body is described. Liner 160 comprises polymeric substrate 162 having control elements 164 embedded or disposed therein. Liner 160 may, for example, be disposed within the working lumen of an elongate body of the present invention, such as working lumen 16 of elongate body 12 of apparatus 10. Polymeric substrate 162 may seal the lumen and preclude contact between the elongate body and bodily fluids. Furthermore, control elements 164 may extend between proximally-disposed control, power, injection, processing, etc., units and a distally-disposed cable that communicates with an articulating element of the present invention. The control elements may comprise, for example, tension wires, electrical wires, optical fibers, fluid transport tubes, etc. The elements may be slidable relative to substrate 162, or may be fixed relative to the substrate. When the position of control elements 164 is fixed relative to the substrate, substrate 162 and elements 164 may be coextruded to form liner 160. It is expected that routing the control elements within a liner will save room, thereby allowing for a larger working lumen for a given delivery profile.

Figure 12:
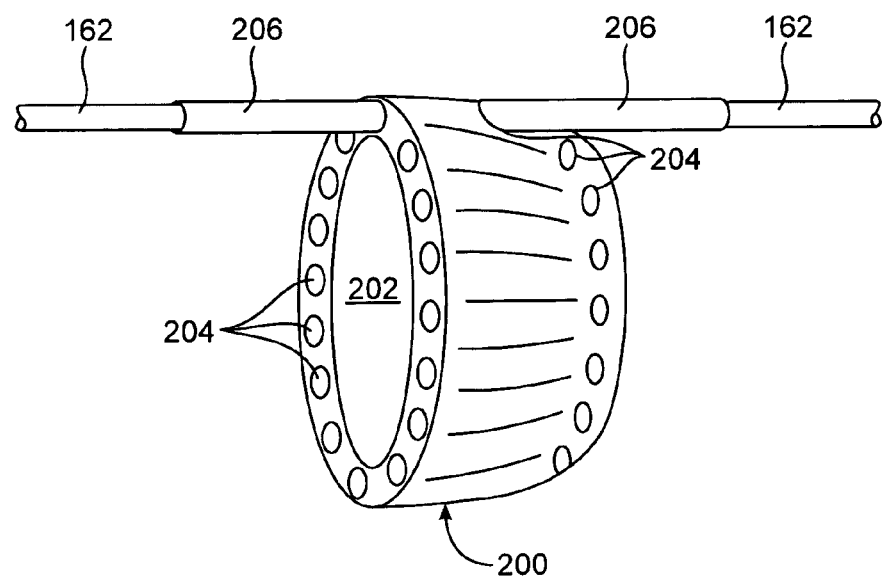
FIG. 12 is a schematic view of an exemplary link of an elongate body having through-holes for passage of control elements.

With reference to FIG. 12, alternative apparatus for routing control elements is described. FIG. 12 illustrates exemplary link 200 for an elongate body. A plurality of such links may be nested within one another to form the elongate body. Steerable and/or shape-lockable elongate bodies formed from a plurality of nested links have been described previously, for example, in Applicant's co-pending U.S. patent application Ser. No. 10/797,485, filed Mar. 9, 2004, which has been incorporated herein by reference. Link 200 comprises working lumen 202 and through-holes 204. Control elements 162 may be routed through the through-holes. In FIG. 12, exemplary control element 162 is illustratively disposed within coil 206. Coil 206 may protect the control element during bending of an elongate body formed from a plurality of links 200. Furthermore, coil 206 may provide superior torqueability and/or pushability to such an elongate body.

One method for obtaining endoluminal access comprises advancing an elongate body or guide, as described above, into a body lumen or other cavity, e.g. advancing the elongate body or guide laparoscopically or endoluminally. The elongate body comprises an articulating element disposed near a distal region thereof, and the exemplary method further comprises articulating the articulating element from a position in-line with a working axis of the elongate body to a position out-of-line or off-axis from the working axis. Articulating the articulating element may expand the articulating element from a reduced delivery configuration to an expanded deployed configuration in a radially extended manner. Furthermore, articulating the element may expose the distal opening of a lumen through which a tool, fluid, suction, etc., may be advanced or withdrawn.

The method may further comprise imaging within the body lumen via an articulated visualization element. Such imaging optionally may be stereoscopic, and the depth of field, field of view, focal point or depth, etc., of such imaging may be altered. Additionally or alternatively, the method may comprise performing diagnostic or therapeutics actions via tools or instruments attached to, or advanced along, an articulated element. The method further may comprise repositioning the articulating element in-line with the working axis of the elongate body and manipulating or removing the elongate body from the body lumen, as well as optionally re-articulating the element. The elongate body may be steered and/or rigidized while obtaining endoluminal access.

Figure 13A:
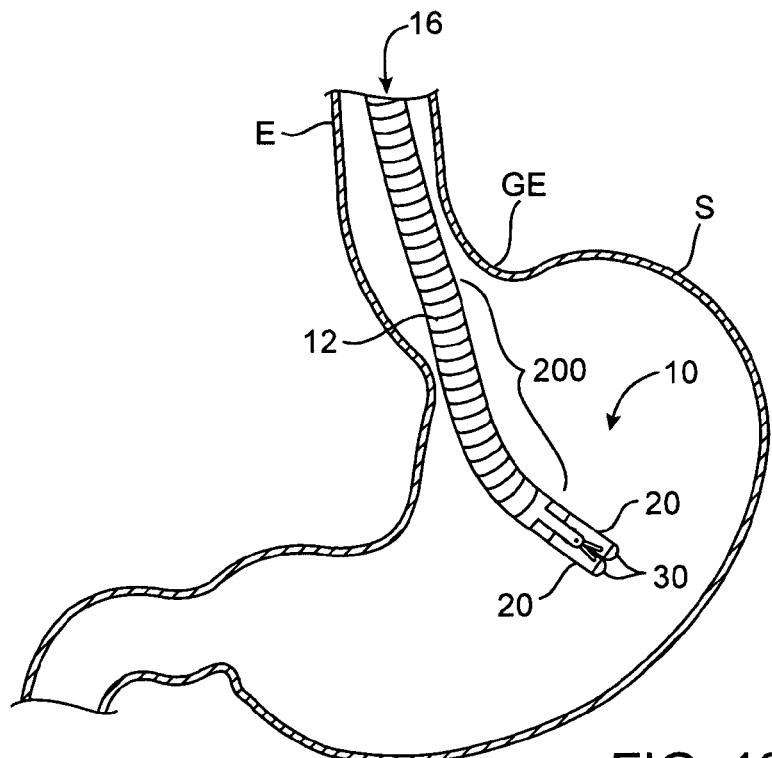
FIGS. 13A-13C are side views, partially in section, of an exemplary endoluminal method and apparatus for obtaining endoluminal access for performing diagnostic and/or therapeutic procedures.

Referring now to FIG. 13, an exemplary endoluminal method and apparatus for obtaining endoluminal access is described. In FIG. 13A, apparatus 10 of FIGS. 1 and 2 is shown with an exemplary elongate body 12 formed from a plurality of links 200 of FIG. 12. Articulating element(s) 20 are disposed at the end of elongate steerable and shape-lockable/rigidizable body 12. Apparatus 10 is advanced per-orally and endoluminally through the patient's esophagus E past gastroesophageal junction GE into stomach S with articulating elements 20 disposed in a low profile delivery configuration. Visualization element 30 may, for example, be positioned on one or more of the articulating elements 20 to provide direct visualization during endoluminal positioning of apparatus 10, as well as to provide direct visualization of tools advanced through lumen(s) 16 of elongate body 12 of the apparatus post-articulation of element(s) 20.

Figure 13B:
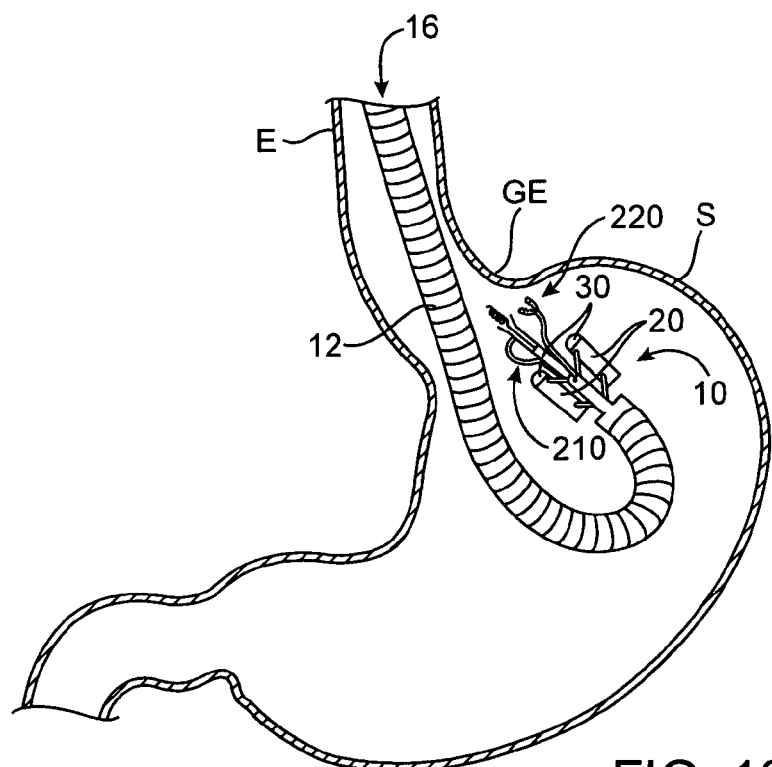
Figure 13C:
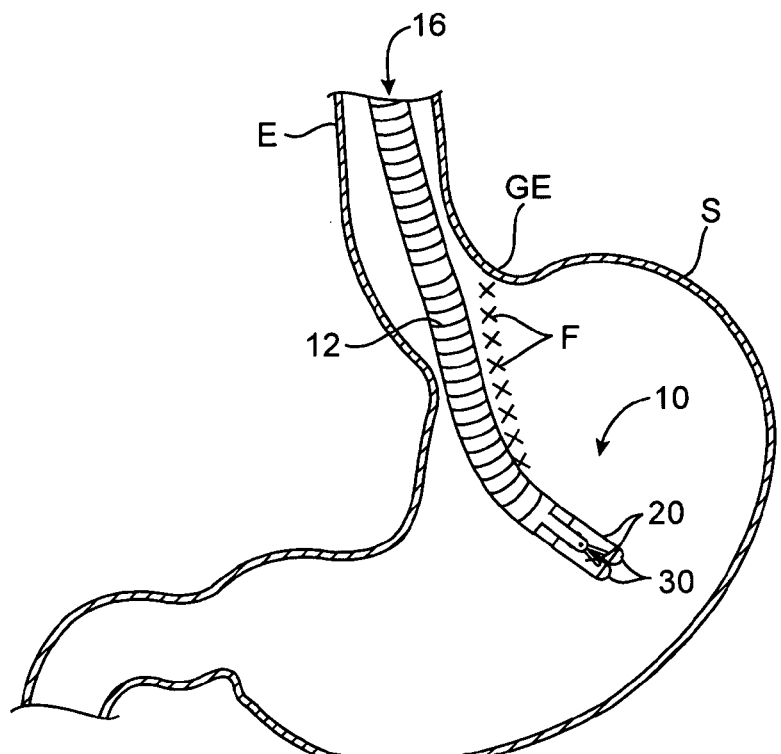

As seen in FIG. 13B, body 12 may be steered, retroflexed, etc., into a desired configuration for diagnosis or treatment. Exemplary endoluminal treatments, such as gastric reduction and treatment of GERD, have been described previously, for example, in Applicant's co-pending U.S. patent application Ser. No. 10/734,562, filed Dec. 12, 2003; and Ser. No. 10/841,233, filed May 7, 2004, both of which are incorporated herein by reference in their entireties. Once properly positioned, element(s) 20 may be articulated off-axis to expose one or more lumens 16 through which additional tools or instruments, such as tissue plication assembly 210 and tissue manipulation assembly 220, may be advanced. As will be apparent, other tools also may be utilized, depending upon the desired diagnostic and/or therapeutic procedure to be performed upon the tissue. As seen in FIG. 13C, after completion of a diagnostic or therapeutic procedure; such as formation, approximation and securement of anterior and posterior tissue folds F to partition stomach S; the apparatus may be returned to a low-profile configuration by retracting the tools or instruments back within lumen(s) 16 and articulating element(s) 20 back into alignment with the longitudinal axis of elongate body 12 of apparatus 10. Apparatus 10 then may be removed from the patient to complete the procedure.

Figure 14:
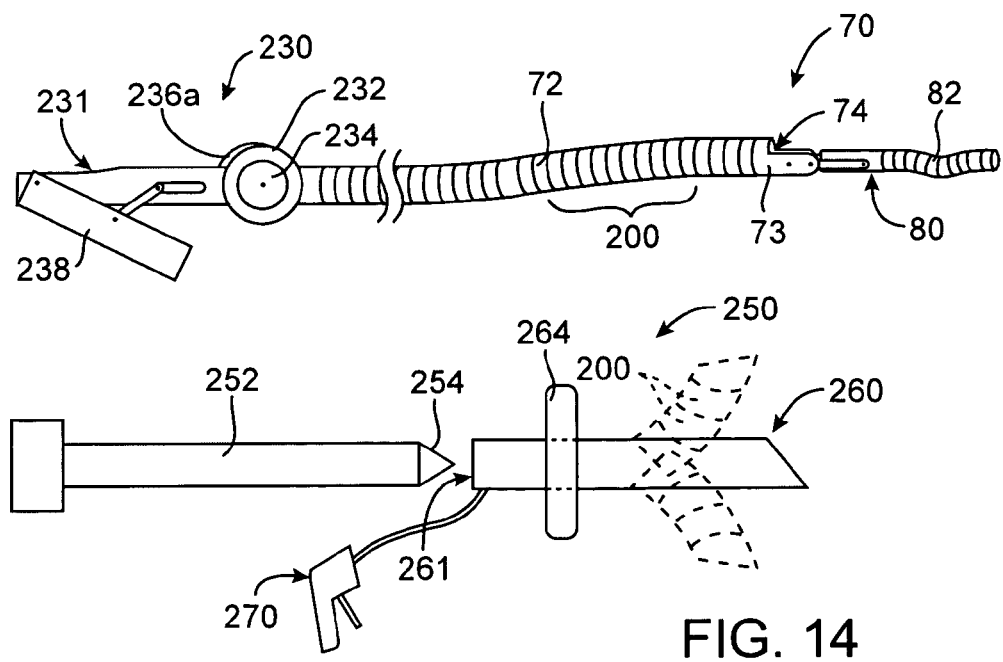
FIG. 14 is a schematic view of exemplary laparoscopic apparatus for obtaining endoluminal access.
Figure 15A:
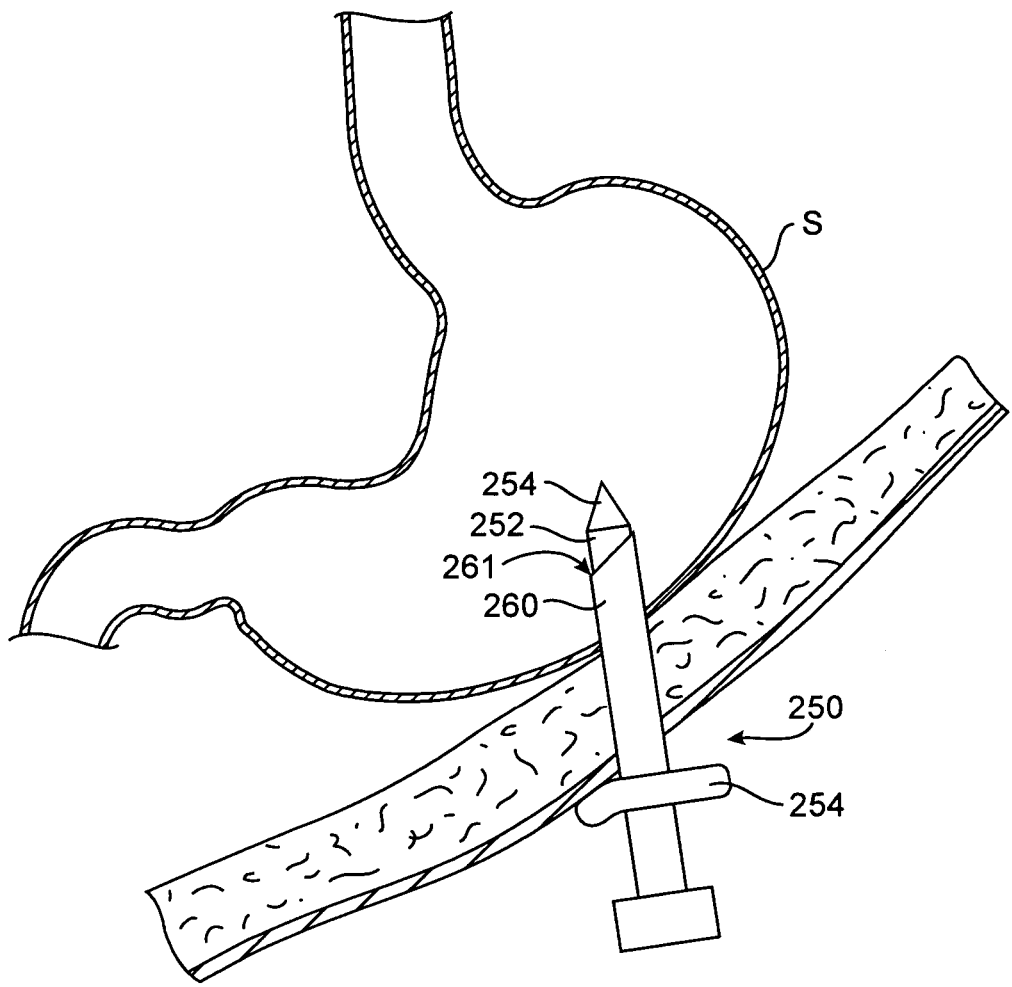
FIGS. 15A and 15B are schematic views, partially in section, of an exemplary method of using the apparatus of FIG. 14 to obtain single port laparoscopic endoluminal access for performing diagnostic and/or therapeutic procedures.
Figure 15B:
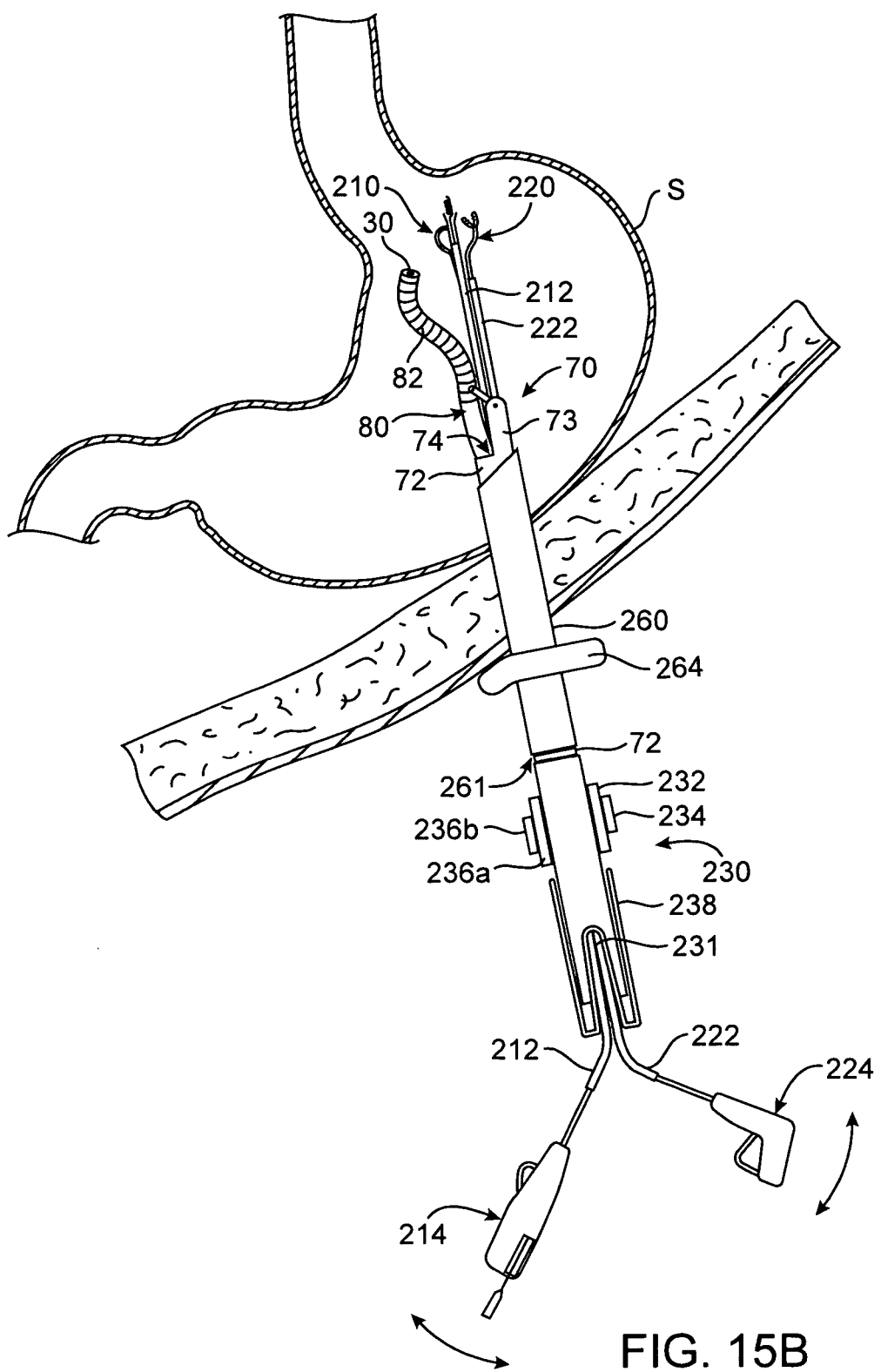

With reference to FIGS. 14 and 15, an exemplary laparoscopic method and apparatus for obtaining endoluminal access is described. In FIG. 14, apparatus 70 of FIG. 6 is shown with an exemplary elongate body 72 formed from a plurality of links 200 of FIG. 12. One or more lumens 74 extend through body 72, and articulating element 80, having four-way steerable shaft 82 and optional visualization element 30, is disposed near distal region 73 of the elongate body. Illustrative control handle 230 is provided to manipulate apparatus 70. Lumen 231 extends through the handle and communicates with lumen(s) 74 of elongate body 72. Knob 232 of handle 230 may facilitate steering of elongate body 72, while knob 234 may control off-axis articulation of element 80, and knobs 236a and 236b (see FIG. 15B) may control four-way steering of shaft 82. Knob 236a may, for example, facilitate steering of shaft 82 along an axis perpendicular to a steering axis controllable via knob 236b. Handle 230 further comprises shape-locking or rigidizing lever 238 for maintaining a configuration of elongate body 72. Steering, off-axis articulation and and/or shape-locking of apparatus 70 with handle 230 preferably is achieved via tensioning wires that extend along elongate body 72 through through-holes 204 of links 200 (see FIG. 12).

Apparatus 70 may be used in conjunction with trocar assembly 250 to perform single-port laparoscopic procedures. Trocar assembly 250 may be any standard or customized trocar assembly and may comprise obturator 252 having sharpened tip 254, as well as trocar 260 having lumen 261 with a universal or other fluid seal therein. Lumen 261 and the fluid seal are configured for passage of obturator 252 therethrough. The lumen and seal are also configured for passage of apparatus 70 or other apparatus therethrough.

Trocar 260 optionally may comprise member 264 for stabilizing the trocar against tissue, as described hereinafter. Member 264 optionally may be expandable and/or inflatable, and may be expandable from a low profile configuration, as shown in dotted profile in FIG. 14, to the illustrated expanded configuration. The optional low profile configuration may facilitate placement of member 264 across the wall of a body lumen or cavity.

Trocar 260 may comprise a substantially rigid tubular shaft, or may be flexible and passively or actively steerable, as illustrated in dotted profile in FIG. 14. When actively steerable, trocar 260 may, for example, be fabricated from a plurality of links 200 and manipulated via optional control handle 270. Additional laparoscopic apparatus and methods, which may be utilized as desired in combination with apparatus of the present invention, are described in Applicant's co-pending U.S. patent application Ser. No. 10/843,682, filed May 10, 2004, which has been incorporated herein by reference.

As seen in FIG. 15A, an incision may be formed through a patient's skin, and trocar 260, having obturator 252 disposed therethrough, may be advanced through the incision directly into stomach S, as shown, or into the peritoneal space. Treatment or diagnosis (e.g., obesity treatment, appendectomy, cholecystectomy or gall bladder removal, etc.) may be performed within the peritoneum (see FIG. 16), or trocar assembly 250 may be further advanced into a body lumen, such as the stomach. In FIG. 15A, sharpened tip 254 of obturator 252 pierces the wall of stomach S, and a distal region of trocar 260 is advanced within the stomach. Obturator 252 then may be removed from lumen 261 of trocar 260, and member 264 optionally may be expanded. If the member is disposed within stomach S, trocar 260 may be retracted such that a position of the trocar is stabilized against the internal wall of the stomach. Alternatively, if the member is disposed exterior to the patient, as in FIG. 15A, the trocar may be advanced such that the position of the trocar is stabilized against the patient's skin or exterior. In FIG. 15, although trocar 260 illustratively has been placed through the antrum of the patient's stomach, it should be understood that the trocar alternatively may be positioned at any other location, as desired.

As seen in FIG. 15B, once trocar 260 has been properly placed, apparatus 70 may be advanced through the trocar into stomach S with articulating element 80 disposed in a low profile delivery configuration. Elongate body 72 then may be steered into a desired configuration for diagnosis or treatment and optionally may be rigidized or shape-locked, e.g., via lever 238, to maintain the desired configuration. Optional visualization element 30 coupled to articulating element 80 may facilitate steering of elongate body 72 into a desired configuration or position. Once apparatus 70 is properly positioned, element 80 may be articulated off-axis to expose one or more lumen(s) 74 through which additional tools or instruments, such as tissue plication assembly 210 and tissue manipulation assembly 220, may be advanced.

Plication assembly 210 illustratively comprises elongate, flexible shaft 212 coupled to control handle 214 for operating the plication assembly. Likewise, manipulation assembly 220 illustratively comprises elongate, flexible shaft 222 coupled to control handle 224 for operating the manipulation assembly. As will be apparent, additional or alternative instruments, such as an endoscope or laparoscope may be utilized. Furthermore, the instruments optionally may be configured for passage through steerable shaft 82 of articulating element 80 to facilitate off-axis use of the instruments. In FIG. 15, shaft 82 illustratively comprises visualization element 30, and procedures performed with assemblies 210 and 220 may be monitored via the visualization element.

After completion of a diagnostic or therapeutic procedure, apparatus 70 may be returned to a flexible, low-profile configuration by releasing lever 238, retracting assemblies 210 and 220 within lumen(s) 74 and articulating element 80 back into alignment with the longitudinal axis of elongate body 72, as in FIG. 14. The apparatus then may be retrieved through trocar 260. Trocar 260 may be removed, and the punctures through the stomach wall and the patient's skin may be sutured closed. In this manner, the apparatus facilitates performance of complex endoluminal or peritoneal procedures through a single laparoscopic access port or trocar. The apparatus preferably comprises both visualization and other diagnostic and/or therapeutic tools. As will be apparent, additional laparoscopic ports optionally may be provided, as desired. Furthermore, instruments advanced through the patient's esophagus optionally may be used in conjunction with laparoscopic endoluminally placed instruments. Furtherstill, apparatus 70 may be advanced across the patient's skin, e.g., into the patient's peritoneum or stomach, without use of an intervening trocar.

Figure 16:
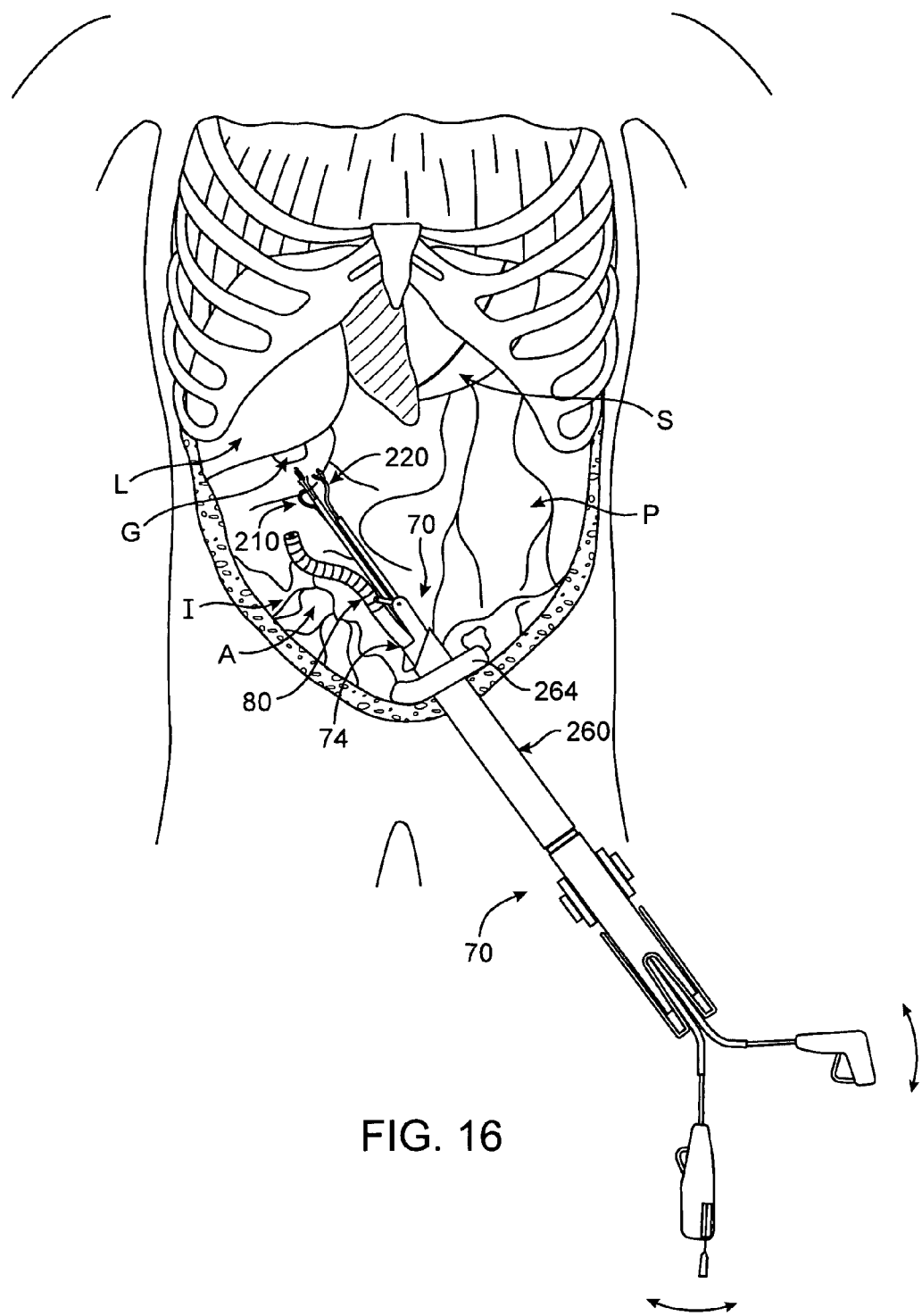
FIG. 16 is a schematic cut-away view of an exemplary method of using the apparatus of FIG. 14 to obtain single port peritoneal access for performing diagnostic and/or therapeutic procedures.

With reference now to FIG. 16, an illustrative method of using the apparatus of FIG. 15 in the peritoneal cavity or space is described. Trocar 260 may be placed through the patient's skin and across the tissue wall within the patient, as described previously, and apparatus 70 may be advanced through the trocar into peritoneal cavity P. In FIG. 16, member 264 of trocar 260 illustratively also is disposed within the peritoneal cavity, and is expanded to stabilize the trocar against the interior wall of the cavity. Articulating element 80 then may be articulated off-axis, and instruments, such as tissue plication assembly 210 and tissue manipulation assembly 220, may be advanced through lumen(s) 74 of apparatus 70 and/or through shaft 82 of element 80 to perform a diagnostic and/or therapeutic procedure within the cavity. Articulating element 80 optionally may comprise visualization element 30 for monitoring procedures performed via apparatus 70. Diagnostic and/or therapeutic procedures may, for example, be performed on the patient's liver L, gall bladder G, stomach S, intestines I, appendix A, etc.

Appendectomy is an exemplary therapeutic procedure that may be performed within the peritoneal cavity. Such a procedure may, for example, proceed as follows. Access to peritoneal cavity P may be gained via an 18-20 mm dilated incision in the umbilicus, similar to a hassan entry. Apparatus 70 then may be introduced through a trocar, such as trocar 260 as in FIG. 16, or may be introduced bluntly through the incision in a rigid state, pre-shaped by the surgeon to allow it to be placed in the direction of the target area. A pneumoperitoneum may be established and maintained to the normal standards for conventional laparoscopy, for example, via an insufflation channel extending through an insufflation lumen 74 of apparatus 70. Visualization element 30 may be connected to a light source and a video monitor exterior to the patient in order to establish visualization, and a proximal section of apparatus 70 optionally may be locked to a standard table-mounted clamp.

Next, apparatus 70 may be steered and re-positioned such that an inspection of the Cecum and appendix A can be completed. Element 80 is articulated off-axis to provide a "top down" view with visualization element 30, wherein the Appendix is centered in the field of view. An operating dissector and scissor are introduced, for example, through first and second lumens 74 of apparatus 70. Utilizing the dissector and scissors as necessary, appendix A is bluntly separated from any adherent omentum or adhesions and mobilized. Depending on positioning of the appendix relative to the cecum, further mobilization may be necessary.

A temporary clamp or suture may be introduced through a third lumen 74 of apparatus 70 and is placed across the appendiceal mesentery in the standard fashion. The appendiceal mesentery is then ligated and divided using, for example, cautery or ligating clips and scissors. Temporary clamps or sutures then may be placed at the base of the appendix if desired. Scissors are used to transect the base of appendix A flush with the clamp or suture. An anchor stitch may be placed to close the remnant base, or it may be left open and secured by inversion within the cecum. Further anchors may be placed to affect a purse string suture at the cecum and invert the stump. The area may be inspected for hemostasis and irrigated/suctioned in the standard fashion for laparoscopy.

Next, the dissector may be affixed to the tip of the appendix, element 80 may be articulated back in-line with the longitudinal axis of elongate body 72, and apparatus 70 may be withdrawn through the umbilicus. Alternatively, an anchor may be placed through the tip of the appendix and the suture end may be grasped via the dissector. Apparatus 70 then may be removed gently from the peritoneal cavity, and the end of appendix A may be pulled through the incision until it can be grasped using a standard surgical clamp. The appendix is delivered through the incision in the standard fashion, and the incision is closed with sutures. It should be understood that the preceding method of removing a patient's appendix utilizing apparatus 70 is provided for the purposes of illustration, and variations or modifications to the method within the scope of the present invention will be apparent to those of skill in the art.

Cholecystectomy is another exemplary therapeutic procedure that may be performed within peritoneal cavity P. Access to the peritoneal cavity again may be gained via an 18-20 mm dilated incision in the umbilicus, similar to a hassan entry. Apparatus 70 may be introduced through a trocar or may be introduced bluntly through the incision in a rigid state, preshaped by the surgeon to allow it to be placed in the direction of the target area. A pneumoperitoneum may be established and maintained to the normal standards for conventional laparoscopy, for example, via an insufflation channel extending through an insufflation lumen 74 of apparatus 70. Visualization element 30 may be connected to a light source and a video monitor exterior to the patient in order to establish visualization, and a proximal section of apparatus 70 optionally may be locked to a standard table-mounted clamp.

Apparatus 70 is steered and positioned such that an inspection of the upper right quadrant can be completed via visualization element 30 of articulating element 80. Element 80 then may be articulated off-axis to provide a "top down" view of the fundus of gallbladder G. If the gallbladder cannot be seen, an operating dissector and scissor or electrosurgical hook may be extended through lumen(s) 74 of apparatus 70, and any adhesions may be removed.

A retracting grasper may be inserted through a lumen 74 of apparatus 70 and firmly affixed and locked to the fundus of gallbladder G. The gallbladder then may be exposed via anterior and lateral traction, for example, in the manner of conventional laparoscopy. Utilizing scissors advanced through apparatus 70 to create an incision in the cystic duct and a self-sealing catheter, an intraoperarative cholangiogram may be performed.

The cystic duct may be isolated using the dissector and an electrosurgical hook, and the cystic artery then may be skeletonized and isolated using a similar technique. The location of the common duct and any unusual arterial branches may be visually verified. The electrosurgical hook may be withdrawn, and ligating ties or clips may be placed on the duct and artery, thereby leaving double closure if desired on each patient side. Scissors may be introduced through apparatus 70 and used to transect the artery and duct, thereby completely mobilizing the gallbladder infundibulum.

The retraction grasper optionally may be maintained at the fundus or may be repositioned centrally along the gallbladder as desired. Utilizing cautery scissors or hook introduced through apparatus 70, as well as the operating dissector for additional traction and dissection, the gallbladder serosa is scored, and the fundus is mobilized in the manner of conventional laparoscopy. The gallbladder bed is inspected and any bleeding areas are cauterized. Irrigation may be used to clean the area and facilitate inspection. Once the gallbladder is completely excised, the grasper may be repositioned for easy removal of the specimen. Element 80 then may be articulated back in-line with the longitudinal axis of elongate body 72, and apparatus 70 may be slowly straightened and withdrawn, pulling gallbladder G along with the locked grasper. Once the gallbladder is visible through the incision, a clamp replaces the grasper, the gallbladder is removed through the umbilicus and the. incision is closed.

It should be understood that the preceding method for performing cholecystectomy utilizing apparatus 70 is provided for the purposes of illustration, and variations or modifications to the method within the scope of the present invention will be apparent to those of skill in the art. Furthermore, alternative methods and procedures utilizing apparatus 70 within peritoneal cavity P, stomach S, or any other region of a patient's body will be apparent to those of skill in the art.

Although various illustrative embodiments are described above, it will be evident to one skilled in the art that various changes and modifications are within the scope of the invention. It is intended in the appended claims to cover all such changes and modifications that fall within the true spirit and scope of the invention.

What is claimed is:

1. Apparatus for obtaining laparoscopic access, the apparatus comprising: a trocar having a lumen; an elongate body adapted for insertion through the trocar lumen, the elongate body having a longitudinal axis and a distal region, the elongate body comprising a plurality of links and at least one tensioning wire for transforming the elongate body from a first, substantially flexible state to a second, substantially rigid state; at least two working lumens extending through the flexible elongate body; and first and second articulating elements near or at the distal region, with the first articulating element pivotally connected to the elongate body near or at its distal region by a first linkage member pivotally connected to a first hinge on the first articulating element and a second hinge on the elongate body; a first visualization element on the first articulating element; a second visualization element on the second articulating element; wherein the first articulating element is movable from an in-line position to an off-axis position relative to the longitudinal axis of the elongate body, and wherein a distal opening of at least one of the working lumens is substantially covered by the first articulating element in the in-line position and is substantially uncovered by the articulating element in the off-axis position.

2. The apparatus of claim 1, wherein the apparatus has a delivery configuration in which the articulating element is aligned with or adjacent to the longitudinal axis of the elongate body, and a deployed configuration wherein the articulating element is articulated off-axis from the longitudinal axis of the elongate body, and wherein the elongate body is configured for insertion through the lumen of the trocar when the apparatus is in the delivery configuration.

3. The apparatus of claim 1 wherein the at least two articulating elements are configured for independent off-axis articulation.

4. The apparatus of claim 1 wherein the at least two articulating elements are configured for coordinated off-axis articulation.

5. The apparatus of claim 1 wherein the first visualization element comprises a fiber optic visualization element.

6. The apparatus of claim 1 wherein the first visualization element comprises a video chip coupled to a signal-processing unit.

7. The apparatus of claim 1 further comprising a light source for illuminating an interior of the body lumen to facilitate visualization with the first visualization element.

8. The apparatus of claim 1 further comprising a housing configured to facilitate articulation of the first articulating element.

9. The apparatus of claim 1, wherein the elongate body is steerable.

10. The apparatus of claim 1, wherein at least one of the first and second the articulating elements further comprises a diagnostic or therapeutic tool.

11. A method for obtaining access to a body lumen or body cavity comprising: placing a trocar through a wall of the body lumen or body cavity; advancing an elongate body into the body lumen or body cavity, with the elongate body having an articulatable element near or at a distal region of the elongate body; moving the articulatable element from a position in-line with or adjacent to a longitudinal axis of the elongate body to a position off-axis relative to the longitudinal axis, to expose a distal opening of a working lumen in the elongate body; stereoscopically viewing a surgical site within the body lumen; and passing a diagnostic or therapeutic tool through the working lumen while the articulatable element is maintained in the off-axis position.

12. The method of claim 11, further comprising expanding the articulatable element from a reduced delivery configuration to an expanded deployed configuration.

13. The method of claim 11 further comprising steering the elongate body within the body lumen or body cavity.

14. The method of claim 11 further comprising rigidizing the elongate body within the body lumen or body cavity.

15. The method of claim 11, wherein the body lumen comprises a stomach.

16. The method of claim 11, wherein the body cavity comprises a peritoneal space.

17. Apparatus for obtaining laparoscopic access, comprising: a trocar having a lumen; an elongate body adapted for insertion through the trocar lumen, the elongate body having a longitudinal axis and a distal region; at least two working lumens extending through the flexible elongate body; and first and second articulating elements pivotally connected to the elongate body near or at the distal region of the elongate body by first and second linkage members; wherein the first articulating element is movable from an in-line position to an off-axis position relative to the longitudinal axis of the elongate body, and wherein a distal opening of at least one of the working lumens is substantially covered by the first articulating element in the in-line position and is substantially uncovered by the first articulating element in the off-axis position; and the first and second articulating elements each having a visualization element, to provide stereoscopic visualization.

18. The apparatus of claim 17, wherein the apparatus has a delivery configuration in which the first articulating element is aligned with or adjacent to the longitudinal axis of the elongate body, and a deployed configuration wherein the first articulating element is articulated off-axis from the longitudinal axis of the elongate body, and wherein the elongate body is configured for insertion through the lumen of the trocar when the apparatus is in the delivery configuration.

19. The apparatus of claim 17 wherein the articulating elements are configured for independent off-axis articulation.

20. The apparatus of claim 17 wherein the articulating elements are configured for coordinated off-axis articulation.

21. The apparatus of claim 17 wherein the first visualization element comprises a fiber optic visualization element.

22. The apparatus of claim 17 wherein the first visualization element comprises a video chip coupled to a signal-processing unit.

23. The apparatus of claim 17 further comprising a light source for illuminating an interior of the body lumen to facilitate visualization with the visualization element on the first articulating element.

24. The apparatus of claim 17 further comprising a housing configured to couple the first articulating element to the elongate body and to facilitate articulation of the first articulating element.

25. The apparatus of claim 17, wherein the elongate body is steerable.

26. The apparatus of claim 17, wherein the elongate body is rigidizable.

27. The apparatus of claim 17, wherein the first articulating element further comprises a diagnostic or therapeutic tool.

* * * * *